US009339626B2

(12) United States Patent
LaBollita et al.

(10) Patent No.: US 9,339,626 B2
(45) Date of Patent: May 17, 2016

(54) SEAL FOR VARIABLE COMPRESSION INTERFACES

(75) Inventors: Steve LaBollita, Rancho Cucamonga, CA (US); Andre M. Rustad, Etiwanda, CA (US)

(73) Assignee: CareFusion 207, Inc., San Diego, CA (US)

( * ) Notice: Subject to any disclaimer, the term of this patent is extended or adjusted under 35 U.S.C. 154(b) by 761 days.

(21) Appl. No.: 12/725,278

(22) Filed: Mar. 16, 2010

(65) Prior Publication Data

US 2011/0226250 A1 Sep. 22, 2011

(51) Int. Cl.
*A61M 16/16* (2006.01)
*A61M 16/20* (2006.01)
*A61M 16/10* (2006.01)
(Continued)

(52) U.S. Cl.
CPC ......... *A61M 16/1045* (2013.01); *A61M 16/208* (2013.01); *A61M 15/02* (2013.01); *A61M 16/06* (2013.01); *A61M 16/105* (2013.01); *A61M 2205/0233* (2013.01)

(58) Field of Classification Search
CPC ............... A61M 16/06; A61M 16/105; A61M 16/1045; A61M 16/208; A61M 15/02; A61M 2205/0233; A61M 16/10; A61M 16/20; A61M 16/22
USPC ........................................ 128/205.12, 205.13
See application file for complete search history.

(56) References Cited

U.S. PATENT DOCUMENTS 3,724,495 A 4/1973 Hartley
4,232,667 A * 11/1980 Chalon ............. A61M 16/1045
128/203.12

(Continued)

FOREIGN PATENT DOCUMENTS

CN 1145263 A 3/1997
DE 102008001844 A1 11/2009
(Continued)

OTHER PUBLICATIONS

Ron J. Thiessen, the Impact of Severe Acute Respiratory Syndrome on the Use of and Requirements for Filters in Canada, Respiratory Care Clinics of North America, Respir Care Clin 12 (2006) pp. 287-306, Copyright 2006, Published by Elsevier Inc. All rights reserved, Mar. 3, 2006—respiratorycare.theclinics.com. Address: 23880 133rd Avenue, Maple Ridge, British Columbia, V4R 2V1, Canada.

(Continued)

*Primary Examiner* — Bhisma Mehta
*Assistant Examiner* — Jenna Zhang
(74) *Attorney, Agent, or Firm* — McDermott Will & Emery LLP

(57) ABSTRACT

The disclosure is directed to an example of a device configured to be in fluid communication with an article. The device includes an element configured to contact the article to form a variable compression interface between the element and the article. The device also includes a seal disposed on the element and at the variable compression interface. The seal is configured to reduce an amount of unwanted fluid leakage at the variable compression interface. An example seal includes a filter media configured to trap unwanted particles attempting to pass through the variable compression interface. In one example, the variable compression interface can be included within a heat and moisture exchange (HME) unit.

19 Claims, 5 Drawing Sheets

(51) Int. Cl.
    *A61M 16/06*        (2006.01)
    *A61M 15/02*        (2006.01)

(56)            References Cited

U.S. PATENT DOCUMENTS

| | | | |
|---|---|---|---|
| 5,471,979 | A | 12/1995 | Psaros et al. |
| 5,577,494 | A * | 11/1996 | Kuypers ............ A61M 16/1045 128/201.13 |
| 5,829,428 | A * | 11/1998 | Walters ............... A61M 16/009 128/200.24 |
| 6,478,026 | B1 * | 11/2002 | Wood ................ A61M 16/0666 128/207.13 |
| 6,550,476 | B1 * | 4/2003 | Ryder ................... A61M 16/16 128/201.13 |
| 8,505,537 | B2 | 8/2013 | Persson |
| 2006/0219243 | A1 | 10/2006 | Walstrom |
| 2007/0283962 | A1 * | 12/2007 | Doshi .................... A62B 23/06 128/206.15 |
| 2008/0302365 | A1 | 12/2008 | Cohen et al. |
| 2009/0014007 | A1 | 1/2009 | Brambilla et al. |
| 2009/0301474 | A1 * | 12/2009 | Korneff ............ A61M 16/1045 128/201.13 |
| 2009/0301476 | A1 | 12/2009 | Korneff et al. |
| 2009/0301477 | A1 * | 12/2009 | Pierro ............... A61M 16/1045 128/201.13 |

FOREIGN PATENT DOCUMENTS

| | | | |
|---|---|---|---|
| EP | 1609499 | A1 | 12/2005 |
| JP | 2010524614 | A | 7/2010 |
| RU | 2248813 | C2 | 3/2005 |
| RU | 2350376 | C2 | 3/2009 |
| SU | 140333 | A1 | 11/1961 |
| WO | WO-2008070929 | A1 | 6/2008 |
| WO | WO-2008132222 | A2 | 11/2008 |
| WO | WO-2009149284 | A1 | 12/2009 |
| WO | WO-2009149289 | A1 | 12/2009 |

OTHER PUBLICATIONS

Search Report for International Application No. PCT/US2011/028456 mailed Nov. 25, 2011 (5 pages).
Written Opinion for International Application No. PCT/US2011/028456 mailed Nov. 25, 2011 (4 pages).
First Office Action No. 61765 in Mexican Patent Application No. MX/a/2012/010280.
Second Office Action No. 77687 in Mexican Patent Application No. MX/a/2012/010280.
Chinese Office Action in Chinese Application No. CN201180012547.8 dated Oct. 20, 2014, 10 pages including English translation.
Japanese Office Action in Japanese Application No. 2013-500146 dated Nov. 11, 2014, 11 pages including English translation.
Russian Office Action in Russian Application No. 2012138170, dated Jan. 12, 2015, 9 pages.
Third Office Action in Mexican Application No. MX/a/2012/010280 dated Jan. 13, 2015, 6 pages.
Partial Supplementary European Search Report for European Application No. 11756831.1, dated Mar. 3, 2015, 6 pages.
Chinese Second Office Action for Application No. 201180012547.8, dated Apr. 29, 2015, 8 pages.
Russian Decision to Grant for Application No. 2012138170, dated May 20, 2015, 15 pages.
Extended European Search Report for Application No. 11756831.1, dated Jul. 23, 2015, 14 pages.
Fourth Mexican Office Action for Application No. MX/a/2012/010280, mailing date unknown but received Aug. 6, 2015, 4 pages.
Japanese Office Action for Application No. 2013-500146, dated Aug. 4, 2015, 13 pages.
Chinese Decision to Grant for Application No. 201180012547.8, dated Sep. 1, 2015, 6 pages with Machine Translation.

* cited by examiner

SEAL FOR VARIABLE COMPRESSION INTERFACES

BACKGROUND

Clinicians often use ventilators or breathing circuits to assist patient breathing or to otherwise treat respiratory ailments. Ventilators and breathing circuits provide mechanical assistance to patients having trouble breathing on their own and are used to deliver gases and medications. A breathing circuit may be coupled to or include a positive pressure source, such as a container of a pre-compressed gas or a ventilator, to deliver a flow of pressurized gases to the lungs of a patient. When the overpressure is released, the patient will exhale due to the elasticity of the lungs (in many devices the sequence can be reversed, i.e., a patient attempting to exhale during the overpressure can cause the overpressure to release). At times, the breathing circuit may be a simple, hand-operated bag valve mask to fit over a patient's nose, mouth or both. Some breathing circuits are more complicated and can include a set of additional breathing components, such as nebulizers, heat and moisture exchange (HME) units, and others, disposed between the pressure source and patient.

Breathing circuits are robust but may contain leaky interfaces at locations where components are coupled to the patients, such around masks, or between chambers within the components themselves, such as within HME units. These interfaces are of often leaky as a result of variable compressions between elements of the interface. Variable compression interfaces share the common feature that they provide likelihood for ambient air or other gases to unintentionally mix with the pressurized gases because the interfaces can be leaky. Ambient air or other gases introduced into the circuit can contain unwanted airborne products such as microbials that can spread to the patient. Additionally, leaky interfaces can spread microbials from the patient to the caregiver.

Leaky interfaces that result in unintended mixing of fluids and unwanted penetration of microbials are not limited to breathing circuits. Another example of a variable compression interface includes a duck bill or wiper seal interface with a patient often used with a surgical trocar, which provide an entry point to introduce laparoscopic instruments into a patient to provide a less invasive surgery. Additional examples of variable compression interfaces can be readily determined that reduce the efficiency of fluid flow or permit the penetration of unwanted particles.

SUMMARY

This summary introduces a selection of concepts in a simplified form that are further described below in the Detailed Description. This summary is not intended to identify key or essential features of the claimed subject matter, and it is not intended to limit the scope of the claimed subject matter.

One aspect of the disclosure is directed to an example of a device configured to be in fluid communication with an article. The device includes an element configured to contact the article to form a variable compression interface between the element and the article. The device also includes a seal disposed on the element and at the variable compression interface. The seal is configured to reduce an amount of unwanted fluid leakage at the variable compression interface. An example seal includes a filter media configured to trap unwanted particles attempting to pass through the variable compression interface. In one example, the variable compression interface can be included within an HME unit. In another example, the variable compression interface can be formed between a patient and a mask.

Another aspect of the disclosure is directed to an example of an HME unit. The HME unit includes a housing that forms a first port, a second port, and an intermediate section extending between the first port and the second port. The intermediate section defines first and second flow paths fluidly connecting the first port and the second port. The intermediate section includes a heat and moisture retaining media along the first flow path. The housing includes a valve mechanism having an element forming an aperture, an obstruction member, and a seal. The obstruction member is movably retained within the housing and transitionable between a first point of travel and a second point of travel. The obstruction member at the first point of travel forms a variable compression interface with the element and closes the second flow path to direct fluid-flow through the first path. The obstruction member at the second point of travel permits the fluid-flow through the second flow path. The seal comprises a filter media and is disposed on at least one of the obstruction member and the element at the variable compression interface.

Another aspect of the disclosure is directed to an example of a breathing circuit suitable for use with a patient. The breathing circuit includes a positive pressure fluid source, a termination device configured to interface with the patient, and a component fluidly coupling the positive pressure fluid source to the termination device. The component includes a housing and a valve mechanism. The housing has a first port fluidly coupled to the positive pressure source, a second port fluidly coupled to the termination device, and an intermediate section extending between the first port and the second port. The intermediate section of the housing defines first and second flow paths fluidly connecting the first port and the second port. The valve mechanism is disposed within the intermediate section of the housing. The valve mechanism includes an element forming an aperture, an obstruction member, and a seal. The obstruction member is movably retained within the housing and transitionable between a first point of travel and a second point of travel. When the obstruction member is at the first point of travel, it forms a variable compression interface with the element and closes the second flow path to direct fluid-flow through the first path. When the obstruction member is at the second point of travel, it permits fluid-flow through the second flow path. The seal includes a filter media and is disposed on at least one of the obstruction member and the element at the variable compression interface.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, any directional terminology used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims. It is also to be understood that the features of the various exemplary embodiments described herein may be combined with each other, unless specifically noted otherwise.

Figure 1A:
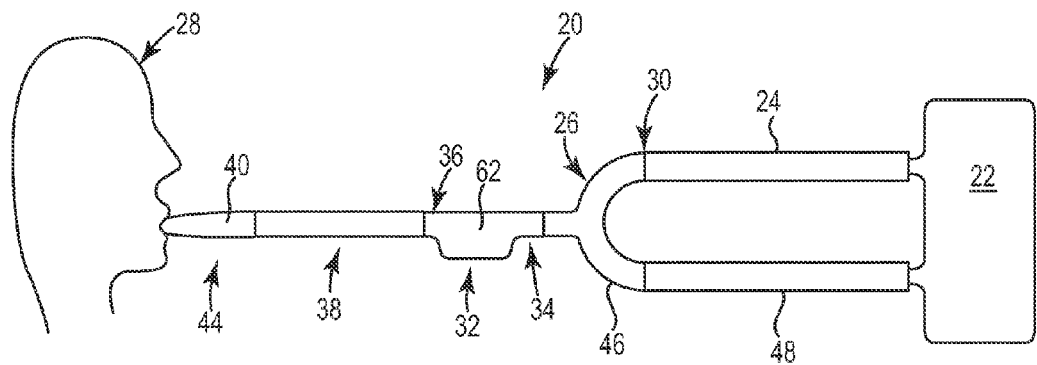
FIG. 1A is a simplified illustration of a breathing circuit, which provides but one example of a suitable environment including features of the present disclosure.

FIG. 1A illustrates an example breathing circuit 20 that includes principles of the present disclosure. The breathing circuit 20 is but one example of a breathing circuit, and a breathing circuit is but one example of an environment suitable for including the principles of the present disclosure. The disclosed principles that are described with reference to the example breathing circuit 20 can be adapted to suit other environments having compression interfaces, which can suffer from leaks that can result in contamination, such as laparoscopic surgery as well as other examples not necessarily related to clinical care. The breathing circuit 20 includes a number of components fluidly coupled together as described below. A ventilator 22 is coupled to a removable ventilator tube 24 to deliver compressed gases, such as air, oxygen, or the like, from the ventilator 22 toward a patient 28. The ventilator tube 24 connects with a Y-connector 26 at an input port 30. The Y-connector 26 is coupled to an HME unit 32 proximal port 34. The HME unit 32 can be a bypass type HME unit. A distal port 36 of the HME unit 32 is connected to a patient tube 38, and the patient tube 38 is coupled to a termination device 44 such as an endotracheal tube 40 or the like. The Y-connector 26 also includes an output port 46 coupled to the ventilator 22 with another ventilator tube 48, that is configured to receive the patient's exhale. The breathing circuit 20 can contain additional components not shown. One such component is a nebulizer that delivers aerosolized medication intended for the patient 28. Another component could be a metered dose inhaler. Other components known and unknown can be included in the breathing circuit 20.

Figure 1B:
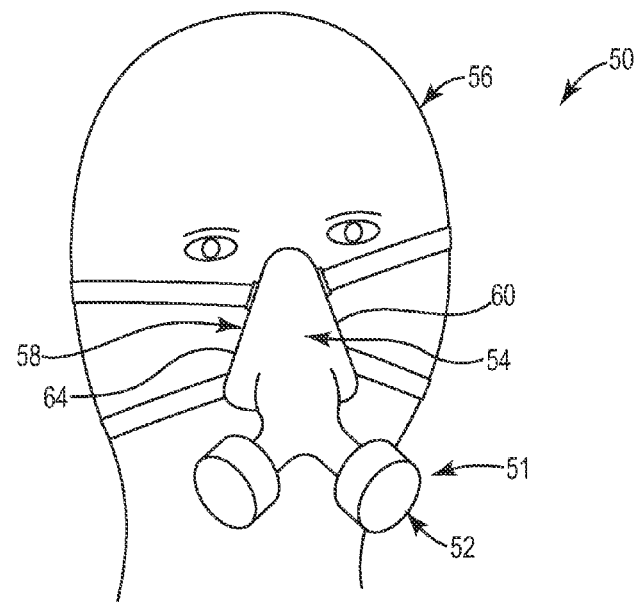
FIG. 1B is a simplified illustration of another example of a breathing circuit, which provides but another example of a suitable environment including features of the present disclosure.

FIG. 1B illustrates but another example breathing circuit 50 including a respirator-type mask 51. The respirator-type mask 51 includes a respirator device 52, which can include filter canisters as shown or simply a filtered input, and is configured to receive pressurized gases or to passively receive air. The respirator 52 is coupled to a mask portion 54 to interface with a user 56. The mask portion 54 includes a lip 60 that is configured to interface with the user 56 at the nose and mouth region 58 of the face.

The breathing circuits 20, 50 include variable compression interfaces where parts of the components can connect to each other, such as a variable compression interface 62 within the HME unit 32 (in FIG. 1A) or where the components connect to the user or patient, such as a variable compression interface 64 where the lip 60 meets the user's/patient's facial region 58 or other skin or tissue (in FIG. 1B). These interfaces include variable compressions as a result of outcome of normal tolerances in manufacturing of the components or the parts of the components, deviations from planar geometry, variations in the durometer or recovery of elastomeric materials, and variations in a patient's anatomy. These variable compression interfaces 62, 64 are provided with a seal described below.

Figure 2:
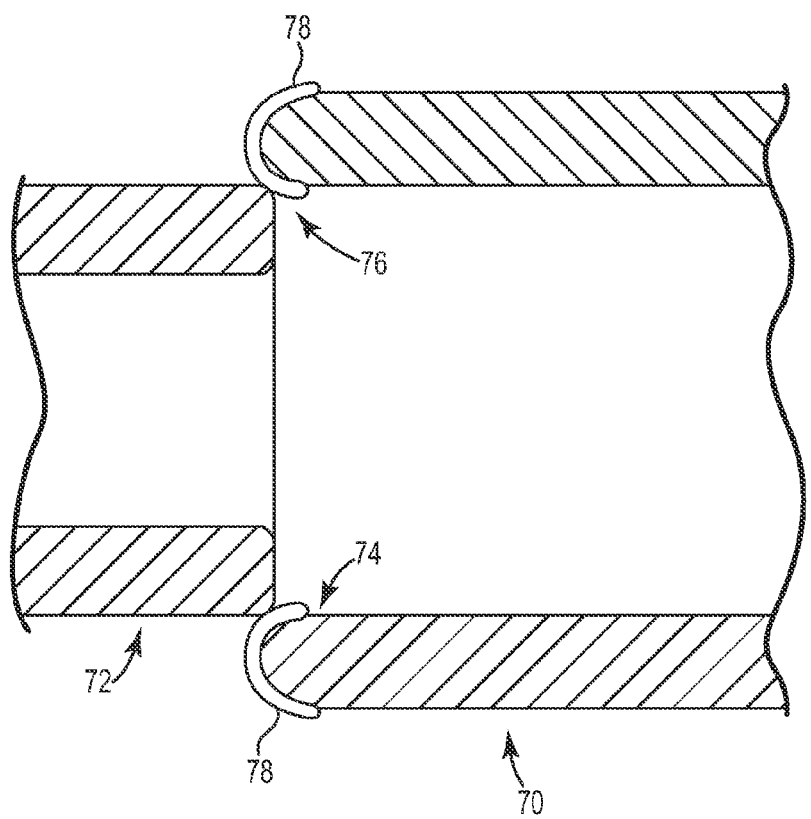
FIG. 2 is a schematic drawing illustrating a device forming a variable compression interface in accordance with principles of the present disclosure.

FIG. 2 illustrates an example constructed in accordance with the present disclosure. More particularly, FIG. 2 illustrates a device 70 that is in fluid communication with an article 72 and constructed in accordance with the principles of the present disclosure. In a first example, the device 70 is the mask portion 54 and the article 72 is the patient's facial region 58 near the nose and mouth of FIG. 1B. In a second example, the device 70 can be a duck bill or wiper seal and the article 72 is a surgical trocar, or the like. The first and second examples are not exhaustive of the possible implementations of the device 70 and are meant only for illustration. The device 70 includes an element 74 configured to contact the article 72 to form a variable compression interface 76 between the element 74 and the article 72. With reference to FIG. 1B, the element 74 is the lip 60 of the mask 54 in the first example. The variable compression interface 76 between the element 74 and the article 72 is not fluid tight by itself, and the variable compression interface 76 includes unwanted fluid leakage. The device 70 also includes a seal 78 disposed on the element 74 and at the variable compression interface 76. The seal 78 is configured to reduce an amount of the unwanted fluid leakage at the variable compression interface 76. The seal 78 comprises a filter media and is described below.

Figure 3A:
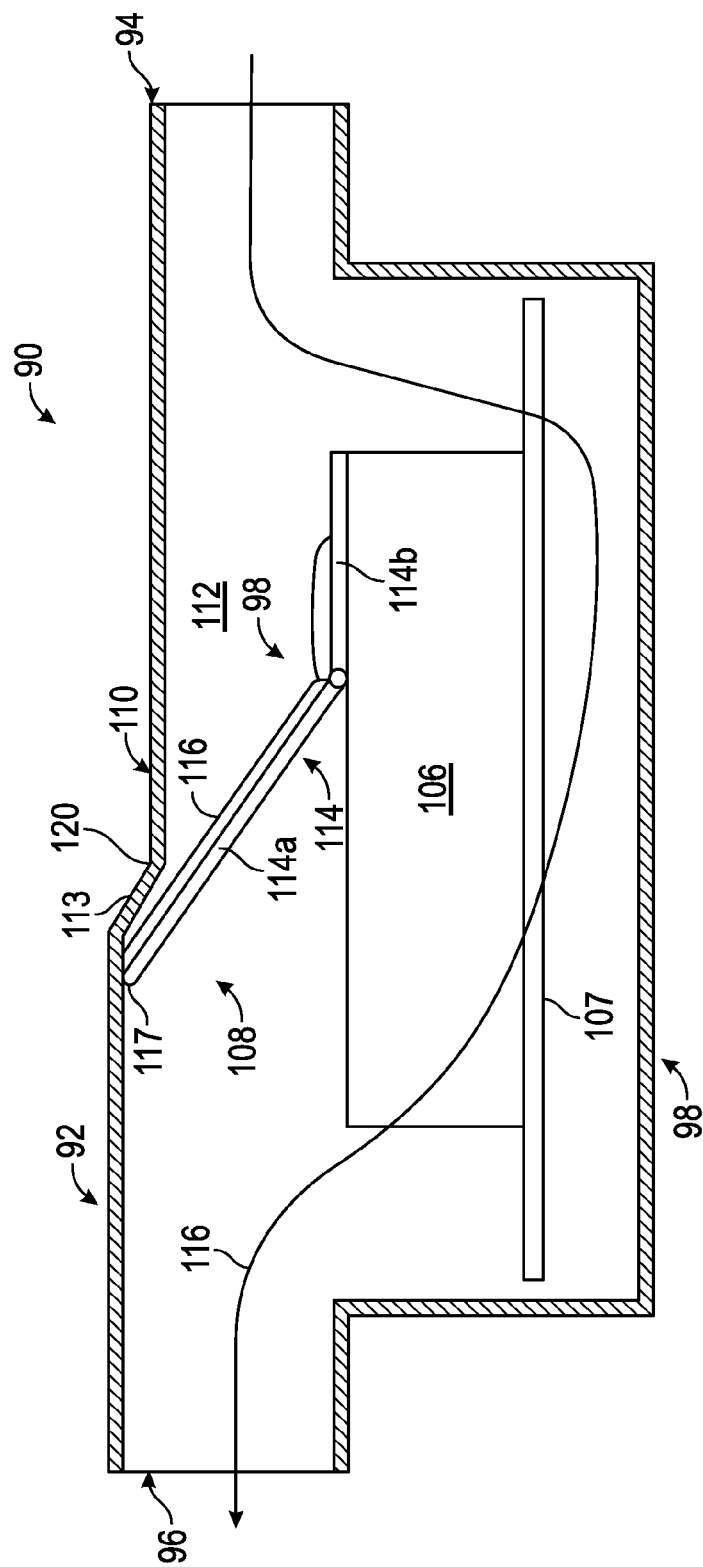
FIG. 3A is a schematic view illustrating a component of the circuit of FIG. 1 that is in accordance with the principles of the present disclosure and in a first configuration.
Figure 3B:
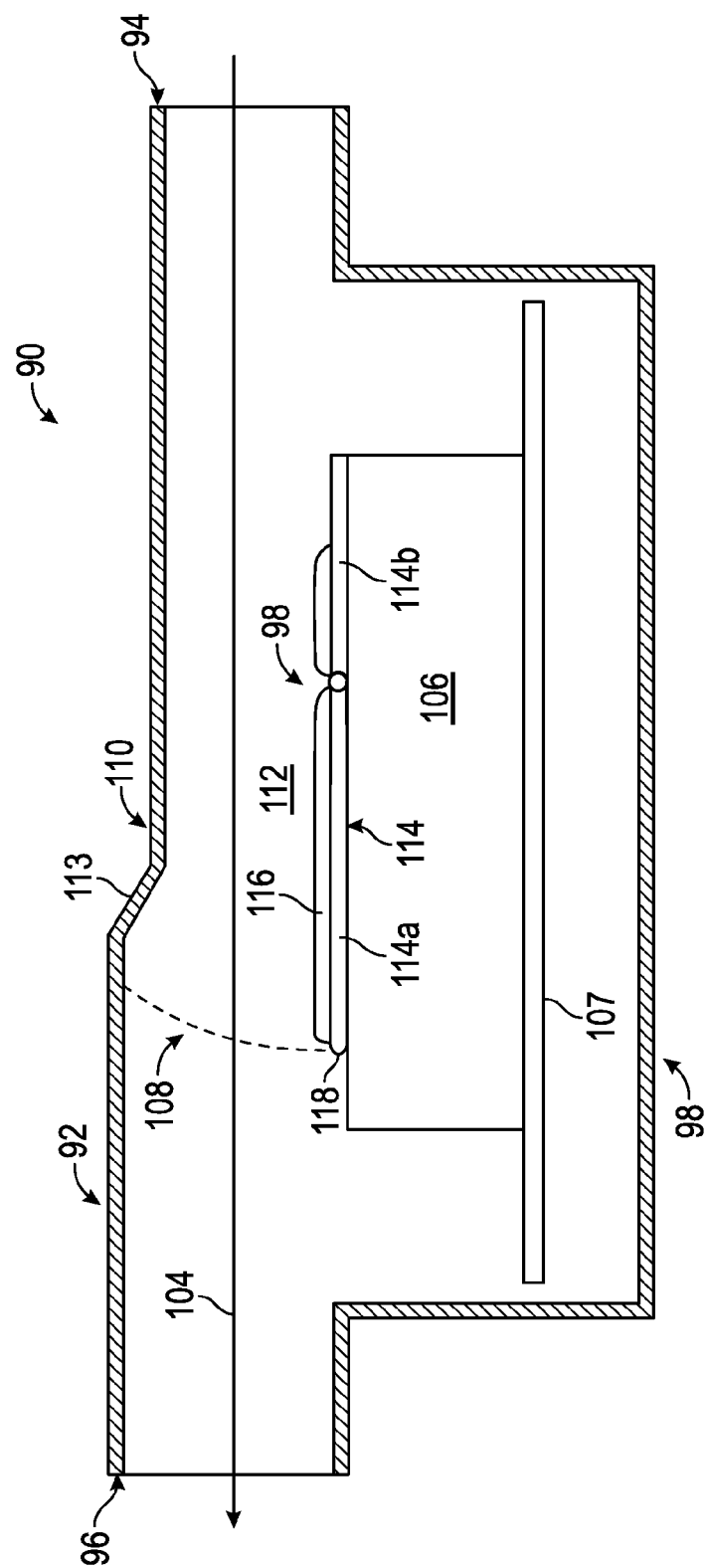
FIG. 3B is a schematic view illustrating the component of FIG. 3A in a second configuration.

FIGS. 3A and 3B illustrate another example constructed in accordance with the present disclosure. More particularly, FIGS. 3A and 3B illustrate an example of an HME unit 90, or more particularly a bypass-type HME unit; constructed in accordance with the principles of the present disclosure, which also includes a variable compression interface. The HME unit 90 includes a housing 92 that forms a first port 94, a second port 96, and an intermediate section 98 extending between the first port 94 and the second port 96. The intermediate section 98 defines a first flow path 102 and a second flow path 104 fluidly connecting the first port 94 and the second port 96. The intermediate section 98 includes a heat and moisture retaining media, or HME media 106, and at times can include a secondary filter 107, along the first flow path 102. The housing 92 includes a valve mechanism 108 having an element 110 forming an aperture 112, having a radially extended ridge 113, an obstruction member 114, having an arm 114a pivotably coupled to a base 114b, and a seal 116. The obstruction member 114 is movably retained within the housing 92 and is transitionable between a first point of travel 117 (shown in FIG. 3A) and a second point of travel 118 (shown in FIG. 3B). The arm 114a of the obstruction member 114 at the first point of travel 116 forms a variable compression interface 120 with the ridge 113 of the element 110 and closes the second flow path 104 to the obstruction member 114 at the second point of travel 118 permits the airflow through the second flow path 104. The seal 116 comprises a filter media and is disposed on at least one of the obstruction member 114 and the element 110 at the variable compression interface 120, and is similar to the seal 78 in the above-described example corresponding with FIG. 2.

During operation of the bypass-type HME unit 90 in a breathing circuit, the first port 94 receives the pressurized gases from a pressure source and in one example corresponds to the proximal the port 34 of the HME unit 32 of FIG. 1. The second port 96 passes the pressurized gases toward the patient 28 and in the example corresponds to the distal port 36 of the HME unit of FIG. 1. When the bypass-type HME unit 90 is set to HME mode as indicated in FIG. 3A, the valve mechanism 118 closes the second flow path 104 and the pressurized gases are directed through the first flow path 102. Gases will travel through the HME media 106 and the secondary filter 107 to the second port 96 to the patient. The patient's exhale will travel in the reverse direction of the first flow path 102. Heat and moisture from the exhale will become trapped with the HME media 106, which can be returned to the patient once the application of pressurized gases are resumed. The seal 116 reduces an amount of unwanted fluid penetrating the valve mechanism when the unit 90 is in the HME mode.

When the bypass-type HME unit is transitioned into bypass mode as indicated in FIG. 3B, the valve mechanism 118 opens the second flow path 104. The valve mechanism 118 can leave the first flow path 102 open, because the fluid flow will substantially follow the path of least resistance, i.e., the unobstructed second flow path 104. Tests indicate that at least 95%, and often at least 98%, of the gases in the bypass-type HME unit 90 pass through the second flow path 104 in the bypass mode. The bypass mode is particularly suitable for delivering aerosolized medications to the patient, such as from a nebulizer or from a metered dose inhaler, without having to break the breathing circuit or without having to contend with the HME media 106 and secondary filter 107 obstructing the delivery of the medications.

Traditional mechanisms or seals used to reduce fluid leaks or create fluid-tight seals in general are ineffective at the variable compression interface 120 to reduce an amount of unwanted fluid leakage, improving the protection from penetration of microbials through gaps at the interfaces, or both. The costs involved in manufacturing tighter or better fitting interfaces are prohibitively expensive. The costs incurred in significantly improving manufacturing tolerances or using stronger, better fitting materials are higher than optimal for a disposable device, and the extra costs would likely be passed on to the patient or whomever was responsible for paying for the patient's care. Typical less expensive means used to stop leaks, such as O-rings and gaskets disposed at the variable compression interfaces, have been demonstrated in experiments as often not effective enough to reduce unwanted leakage and the penetration of microbials. For example, O-rings and gaskets can be difficult to fit in bypass type HME units 90. Generally, amount of force of the element 110 at the variable compression interface 120 to close the second flow path 104 is often too small to properly compress O-rings and many gaskets to form an effective seal. In order to make the HME unit 90 stronger to accommodate the extra forces to properly compress the O-rings, prohibitively more expensive parts and manufacturing techniques are used. Still further, microbials gather on O-rings and gaskets at the variable compression interface 120 when the second flow path 104 is closed, and these microbials are often blown into the breathing circuit causing contamination.

Seal 116 is constructed from a compressible filter media and provides a relatively inexpensive solution to the problem of unwanted leaks and penetration of microbials. For example, bypass type HME units 90 were tested according to ISO 23328-1 with a sodium chloride aerosol having a diameter of 0.3 microns and a particle detector. The test data for HME units with an O-ring or gasket at the interface demonstrated variable and uncontrollable leaks that could not support a filtration claim according to industry standards. HME units having a seal including the compressible filter media, however, provided an improved interface that allowed support for label claims of filtration consistent with guidelines of the Food and Drug Administration.

Such compressible media include a medical-grade, non-woven filter fabric. The non-woven filter fabric is locally compressible under slight force and will modify shape to fit between the obstruction member 114 and the element 110 at the variable compression interface 120 under typical biasing forces used to close the second flow path 104. Thus, typical HME units 90 should not incur a significant redesign or expensive parts. Further, the seal 116 also protects from the penetration of microbials. For example, the filter media disposed within the variable compression interface provides an improved means of trapping unwanted fluid-borne particles in the fluid that does manage to penetrate the seal 116. Additionally, the filter media serves to trap and hold the particles, and will reduce the amount of particles passing into the breathing circuit when the second fluid path 104 is open. The filter media can be provided with an electrostatic charge that operates as a force to keep particles trapped within the filter.

As described in this example, device can include the valve mechanism or the HME device, an element can be the obstruction member 114 configured to contact the article, or element 110 forming the aperture 112 to form the variable compression interface 120 between the element and the article. The seal includes the filter media disposed on the element, such as the obstruction member 114 and at the variable compression interface 120.

Figure 4:
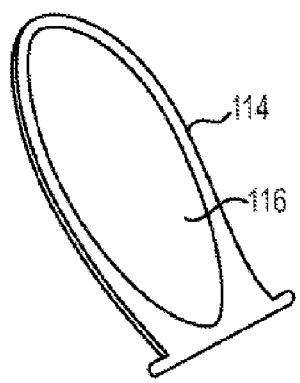
FIG. 4 is a schematic perspective view illustrating a feature of the component of FIG. 3A.

FIG. 4 illustrates a perspective view of the obstruction member 114 from the HME unit 90 having an affixed seal 116 comprising a filter media. In one example, the filter media is constructed from readily-available non-woven fibers, such as polypropylene acrylic having an electrostatic charge, where the fibers are bonded together into a sheet or web. The obstruction member 114 can be constructed from a polymeric material, such as an acetal, or more often referred to as a polyacetal or even polyoxymethylene, which can be sold under the trade designation of Delrin and available from E.I du Pont de Nemours and Company, often referred to as simply DuPont, of Wilmington, Del.

Additional components of the HME unit 90 can be constructed in a variety of configurations, and a few examples of these configurations are described here. The housing of the HME unit 92 can be constructed from a polymeric material that can be dissimilar to the polymeric material used in the obstruction member 114. For example, the housing can be constructed from a thermoplastic such as a styrene-butadiene block copolymer. The seal 116 can be affixed to the obstruction member 114 with a medical grade adhesive. The HME media 106 is often constructed from a resilient or flexible polymer foam treated with a hygroscopic salt, such as polyurethane foam treated with calcium chloride. The secondary filter 107, which can be used in conjunction with the HME material 106 to trap unwanted particles in the first flow path, can be constructed from the same material used in the seal 116. The valve mechanism 108 as shown in the example is a gate valve having a gate hinged on a pin corresponding with the obstruction member 114 and a valve inlet corresponding with the element 110 forming the aperture 112. Other types of valve devices are contemplated, such as ball valves, plunger valves, or the like.

Additionally, the thickness of the filter media used can vary with respect the application of the seal. For example, the seal 78 in the example of FIG. 2 can use a relatively thicker amount of filter media to accommodate for larger gaps at the interface 76 due to greater variances in patient anatomies. The seal 116 in the example of FIGS. 3A and 3B can use a relatively less thick amount of filter media at the interface 120. One skilled in the art can readily apply filter media with a proper thickness in all applications both now know and unknown.

Figure 5:
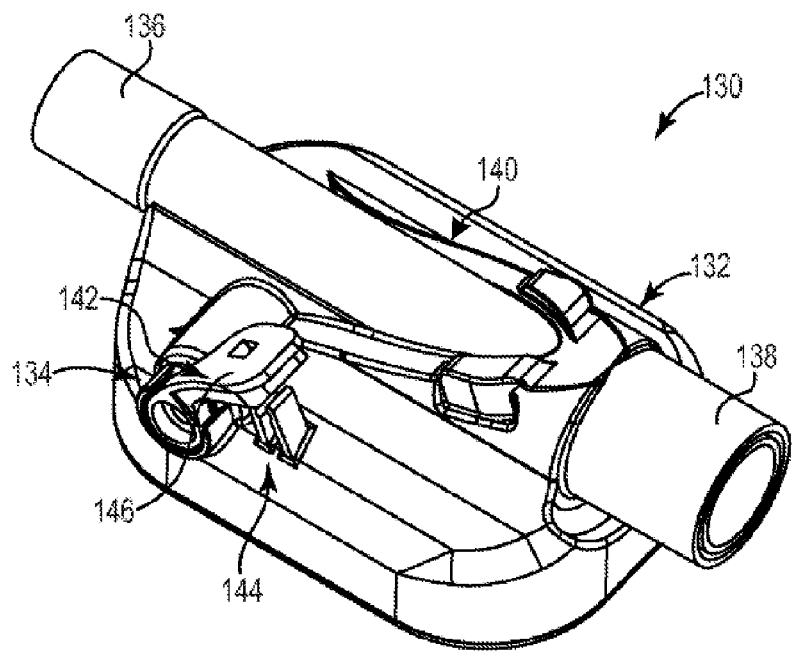
FIG. 5 is a perspective view illustrating an HME unit having a bypass mode and an HME mode, which is suitable for use as a component of the circuit of FIGS. 3A and 3B, in accordance with the principles of the present disclosure.

FIG. 5 illustrates an exemplary HME unit 130 constructed in accordance with the simplified illustrations of FIGS. 3A and 3B. The HME unit 130 includes a housing 132 and a valve mechanism 134 referenced generally. The HME unit 130 also includes features hidden from view such as heat and moisture retaining media (106), secondary filter (107), obstruction member (114) included as part of the valve mechanism 134, and seal (116) also included as part of the valve mechanism 134. The housing 132 forms a ventilator side port 136, a patient side port 138, and an intermediate section 140. The heat and moisture retaining media (106) is retained within the intermediate section 140, with the valve mechanism 134 operating to dictate a pathway through which airflow at least primarily progresses between the ports 136, 138. The valve mechanism 134 includes a biasing member (not shown), such as a torsional spring, that biases the obstruction member (114) to the first point of travel to form a variable compression interface, and effects the HME mode. The valve mechanism 134 includes an actuator assembly 142 and a locking device 144. The actuator assembly 142 includes an actuator arm 146 rotatably assembled to, and projecting from, the housing 132. Rotation of the actuator arm 146 relative to the housing 132 effectuates transitioning of the obstruction member (114) between points of travel. Thus, the actuator arm 146 is rotatable from the HME position to the bypass position and vice-versa. In this regard, the locking device 144 is configured to interface with and releasably lock the actuator arm 146 in the bypass position.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A device configured to be in fluid communication with an article, the device comprising:
   a housing having a first port, a second port, and an intermediate section; the intermediate section having a first flow path between the first port and the second port, and a second flow path between the first port and the second port, the first flow path separated from the second flow path by a heat and moisture retaining media,
   the housing including a valve mechanism in the intermediate section, the valve mechanism comprising
      an element forming an aperture having a radially extending ridge, and
      an obstruction member, the obstruction member comprising an arm pivotably coupled to a base, the base having a first surface and an opposing second surface, the second surface of the base coupled to the heat and moisture retaining media, the arm having a first surface and an opposing second surface, the arm configured to contact the ridge at a first point of travel; and
   a seal disposed on the first surface of the arm and the first surface of the base, the seal compressed between the ridge and the first surface of the arm at the first point of travel to form a variable compression interface so as to restrict fluid leakage across the variable compression interface between the arm and the ridge,
   wherein the seal comprises a sheet or web of compressible filter media formed of non-woven material configured to (i) conform its shape under biasing forces at the variable compression interface; and (ii) trap particles, attempting to pass across the variable compression interface, in the non-woven material;
   wherein the arm at the first point of travel directs the fluid through the first flow path, and a second point of travel directs the fluid through the second flow path.

2. The device of claim 1 wherein the filter media comprises polypropylene acrylic fibers.

3. The device of claim 2 wherein the filter media comprises an electrostatic charge.

4. The device of claim 1 wherein the article is a heat and moisture exchange unit element.

5. The device of claim 4 wherein the seal is disposed on the obstruction member and the element.

6. The device of claim 5 wherein the seal is affixed to the obstruction member with a medical-grade adhesive.

7. The device of claim 1 wherein the fluid is air.

8. A heat and moisture exchange unit comprising:
   a housing having a first port, a second port, and an intermediate section; the intermediate section having a first flow path between the first port and the second port, and a second flow path between the first port and the second port, the first flow path separated from the second flow path by a heat and moisture retaining media, the housing including
      a valve mechanism in the intermediate section, the valve mechanism comprising
         an element forming an aperture having a radially extending ridge, and
         an obstruction member, the obstruction member comprising an arm pivotably coupled to a base, the base having a first surface and an opposing second surface, the second surface of the base coupled to the heat and moisture retaining media, the arm having a first surface and an opposing second surface, the arm configured to contact the ridge at a first point of travel; and
   a seal disposed on the first surface of the arm and the first surface of the base, the seal compressed between the ridge and the first surface of the arm at the first point of travel to form a variable compression interface so as to restrict fluid leakage across the variable compression interface between the arm and the ridge,
   wherein the seal comprises a sheet or web of compressible filter media formed of non-woven material configured to (i) conform its shape under biasing forces at the variable compression interface; and (ii) trap particles, attempting to pass across the variable compression interface, in the non-woven material;
   wherein the arm at the first point of travel directs the fluid through the first flow path, and a second point of travel directs the fluid through the second flow path.

9. The heat and moisture exchange unit of claim 8 wherein the heat and moisture retaining media includes a resilient foam treated with a hygroscopic salt.

10. The heat and moisture exchange unit of claim 9 wherein the heat and moisture retaining media includes a polyurethane foam treated with calcium chloride.

11. The heat and moisture exchange unit of claim 8 wherein the filter media includes non-woven fibers.

12. The heat and moisture exchange unit of claim 11 wherein the non-woven fibers include an electrostatic charge.

13. The heat and moisture exchange unit of claim 11 wherein the non-woven fibers include a polypropylene acrylic having an electrostatic charge.

14. The heat and moisture exchange unit of claim 11 where the fibers are bonded together into a sheet or web.

15. The heat and moisture exchange unit of claim 8 wherein the obstruction member is a gate valve.

16. The heat and moisture exchange unit of claim 8 wherein the obstruction member is biased against the element with a torsional spring.

17. A breathing circuit for use with a patient, the breathing circuit comprising:
a positive pressure fluid source;
a termination device configured to interface with the patient; and
a component fluidly coupling the positive pressure fluid source to the termination device, the component comprising:
a housing having a first port, a second port, and an intermediate section; the intermediate section having a first flow path between the first port and the second port, and a second flow path between the first port and the second port, the first flow path separated from the second flow path by a heat and moisture retaining media, the housing including
a valve mechanism in the intermediate section, the valve mechanism comprising
an element forming an aperture having a radially extending ridge, and
an obstruction member, the obstruction member comprising an arm pivotably coupled to a base, the base having a first surface and an opposing second surface, the second surface of the base coupled to the heat and moisture retaining media, the arm having a first surface and an opposing second surface, the arm configured to contact the ridge at a first point of travel; and
a seal disposed on the first surface of the arm and the first surface of the base, the seal compressed between the ridge and the first surface of the arm at the first point of travel to form a variable compression interface so as to restrict fluid leakage across the variable compression interface between the arm and the ridge,
wherein the seal comprises a sheet or web of compressible filter media formed of non-woven material configured to (i) conform its shape under biasing forces at the variable compression interface; and (ii) trap particles, attempting to pass across the variable compression interface, in the non-woven material;
wherein the arm at the first point of travel directs the fluid through the first flow path, and a second point of travel directs the fluid through the second flow path.

18. The breathing circuit of claim 17 wherein the positive pressure fluid source includes a ventilator.

19. The breathing circuit of claim 17 wherein the termination device includes a mask.

* * * * *